United States Patent
Gronowitz

Patent Number: 5,440,040
Date of Patent: Aug. 8, 1995

[54] PYRIMIDINE INTERMEDIATES

[75] Inventor: Saló Gronowitz, Lund, Sweden

[73] Assignee: Medivir AB, Huddinge, Sweden

[21] Appl. No.: 613,900

[22] PCT Filed: Jun. 7, 1989

[86] PCT No.: PCT/SE89/00322

§ 371 Date: Jan. 18, 1991

§ 102(e) Date: Jan. 18, 1981

[87] PCT Pub. No.: WO89/12061

PCT Pub. Date: Dec. 14, 1989

[30] Foreign Application Priority Data

Jun. 10, 1988 [SE] Sweden ................ 8802173

[51] Int. Cl.[6] .................. C07D 251/24; C07D 239/22
[52] U.S. Cl. ................... 544/216; 544/245; 544/253; 544/254; 544/255; 544/256; 544/298; 544/309; 544/310; 544/311; 544/317; 544/318; 544/324; 544/325; 544/327
[58] Field of Search ............ 536/23, 24, 28, 29, 536/115; 544/242, 253, 255, 256, 180, 254, 249, 250, 1; 514/49, 50, 51, 256.1

[56] References Cited

U.S. PATENT DOCUMENTS

| | | | |
|---|---|---|---|
| 4,182,859 | 1/1980 | Erhardt | 536/28.54 |
| 4,211,773 | 7/1980 | Lopez et al. | 514/49 |
| 4,666,892 | 5/1987 | Fox et al. | 514/49 |

FOREIGN PATENT DOCUMENTS

| | | | |
|---|---|---|---|
| 325874 | 3/1984 | Australia | . |
| 8804662 | 6/1988 | WIPO | . |

OTHER PUBLICATIONS

Anales de la real Academia de farmacia, vol. 50, (1984), pp. 57–66.
Chemica Scripta (1986) vol. 26, pp. 305–309.
J. Med. Chem. (1988) vol. 31, pp. 1141–1147.
Tetrahedron Letters (1984) vol. 25 No. 2, pp. 201–202.

(List continued on next page.)

Primary Examiner—Douglas W. Robinson
Assistant Examiner—J. Oliver Wilson
Attorney, Agent, or Firm—Birch Stewart Kolasch & Birch

[57] ABSTRACT

The present invention is directed to compounds of formula (I),

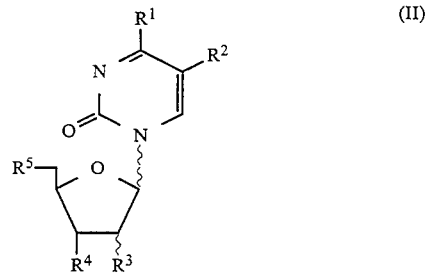

(II)

wherein $R^1$ is OH, $NH_2$; $R^2$ is a heteroaromatic or aromatic substituent; $R^3$ is H, OH, F, $OCH_3$; $R^4$ is H, F, OH or an ether or ester residue thereof, $OCH_3$, CN, C≡CH, $N_3$; $R^5$ is OH or an ether or ester residue thereof including mono-, di- and triphosphate esters ($\alpha$), wherein n is 0 or 1 and M is hydrogen or a pharmaceutically acceptable counterion such as sodium, potassium, ammonium or alkylammonium; and pharmaceutically acceptable salts thereof; and pharmaceutical compositions comprising said compounds can be used for therapeutic treatment of virus infections. The present invention is also directed to compounds of formula (I'),

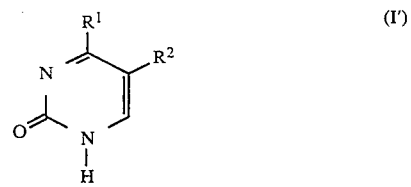

(I')

wherein $R^1$ and $R^2$ are as defined above, as intermediates.

2 Claims, No Drawings

OTHER PUBLICATIONS

Tetrahedron Letters (1984) vol. 25, No. 23, pp. 2431–2434.
Tetrahedron Letters (1980) vol. 21, pp. 2813–2816.
Proceedings Of The 4th International Round Table, Antwerp, 4–6 Feb. 1981, J. Balzarini et al.
Chemical Abstracts, 1987, vol. 107, Abstract No. 58962j, p. 730.
Chemical Abstracts, 1981, vol. 95, Abstract No. 132804m, p. 666.
Chemical Abstracts, 1976, vol. 84, Abstract No. 39219n, p. 86.
Chemical Abstracts, 1976, vol. 84, Abstract No. 17258x, p. 462.
Chemical Abstracts, 1976, vol. 84, Abstract No. 16386a, p. 381.
Chemical Abstracts, 1976, vol. 84, Abstract No. 4892z, p. 416.
Chemical Abstracts, 1972, vol. 76, Abstract No. 25225j, p. 366.
Chemical Abstracts, vol. 104, No. 23, Jun. 9, 1986, see p. 790, abstract 207587h.
Chemical Abstracts, 1964, vol. 64, 1774a.
Chemical Abstracts, 1962, vol. 57, 12482g.
Chemical Abstracts, vol. 98, No. 7, Feb. 14, 1983, see p. 427, abstract 4734p.
Chemical Abstracts, vol. 98, No. 24, Jun. 13, 1983, see p. 17 abstract 209571e.

PYRIMIDINE INTERMEDIATES

FIELD OF THE INVENTION

The present invention relates to novel chemical compounds and pharmaceutically acceptable salts thereof which can be used in therapy for therapeutic treatment of the acquired immuno deficiency syndrome (AIDS) and infections caused by viruses requiring reverse transcriptase for replication, such as human immuno deficiency virus and hepatitis B virus, and also for treatment of virus diseases, such as those of herpes viruses diseases which include common infections and neoplastic diseases, i.e. cancer. The invention also relates to novel precursor compounds constituting a further aspect of the invention.

BACKGROUND OF THE INVENTION

The effects of viruses on bodily functions is the end result of changes occurring at the cellular and subcellular levels. The pathogenic changes at the cellular level are different for different combinations of viruses and host cells. While some viruses cause a general destruction (killing) of certain cells, other may transform cells into a neoplastic state.

Important common viral infections are herpes dermatitis (including herpes labialis), herpes keratitis, herpes genitalis, herpes zoster, herpes encephalitis, infectious mononucleosis and cytomegalovirus infections all of which are caused by viruses belonging to the herpes virus group. Other important viral diseases are influenza A and B which are caused by influenza A and B virus respectively. Another important common viral disease is viral hepatitis and especially hepatitis B virus infections are widely spread. Effective and selective antiviral agents are needed for treatment of these diseases as well as for other diseases caused by viruses. Several different viruses of both DNA and RNA type have been shown to cause tumors in animals. The effect of cancerogenic chemicals can on animals result in activation of latent tumor viruses. It is possible that tumor viruses are involved in human tumors. The most likely human cases known today are leukemias, sarcomas, breast carcinomas, Burkitt lymphomas, nasopharyngeal carcinomas and cervical cancers where RNA tumor viruses and herpes viruses are indicted and papillomas where papilloma viruses are involved. This makes the search for selective inhibitors of tumorogenic viruses and their functions an important undertaking in the efforts to treat cancer.

In the late seventies a new disease was reported, which subsequently was referred to as Acquired Immuno Deficiency Syndrome (AIDS). It is now generally accepted that a retrovirus referred to as HIV (Human Immunodeficiency Virus), formerly known as Human T-cell Lymphotropic Virus (HTLV-III) or Lymphadenopathy Associated Virus (LAV) plays an essential role in the etiology of AIDS. Different types of HIV have been found, such as HIV-1 and HIV-2 and more are likely to be isolated.

AIDS is characterized by a profound immunodeficiency due to low numbers of a subset of lymphocyte-T-helper cells, which are one target for HIV infection. The profound immunodeficiency in AIDS patients makes these patients highly susceptible to a variety of opportunistic infections of bacterial, fungal, protozoal or viral etiology. The etiological agents among viral oppportunistic infections are often found in the herpes virus group, i.e. herpes simplex virus (HSV), Varicella Zoster virus (VZV), Epstein-Barr virus (EBV) and, especially, cytomegalovirus (CMV). Other retroviruses affecting humans are HTLV-I and II and examples of retroviruses affecting animals are feline leukemia virus and equine infectious anaemia virus. Human diseases such as multiple sclerosis, psoriasis, tropical spastic paresis and Kawasaki disease have also been reported to be associated with retrovirus infections. Hepatitis B virus infections cause severe disease such as acute hepatitis, chronic hepatitis, fulminant hepatitis in a considerable number of persons. It is estimated that there are 200 million patients with chronic hepatitis B infection in the world. A considerable number of the chronic cases progress to liver cirrosis and liver tumours. In some cases the hepatitis infections also take a rapid and severe course as in fulminant B hepatitis with about 90% mortality. At present there is no known effective treatment against hepatitis B infections. The replication of hepatitis B virus is similar to that of retroviruses and it contains the same essential viral reverse transcriptase activity.

GENERAL OUTLINE OF THE INVENTION

A great number of nucleoside analogues exhibit several antimetabolic activities. They do so by substituting for or competing with the naturally occuring nucleosides. Recently, some nucleoside analogues have been described, which inhibit in cell culture the multiplication of human immunodeficiency virus (HIV, also called HTLV-III, LAV) the causative agent of AIDS and AIDS-related complex (ARC).

WE have now found that activities for inhibition of herpes multiplication are exhibited by nucleoside analogues, in which the pyrimidine bases are substituted in the 5-position by a heteroaromatic, or aromatic substituent. The nucleoside analogues may be either alpha- or beta-anomers.

DISCLOSURE OF THE INVENTION

The present invention relates to new compounds of the formula I

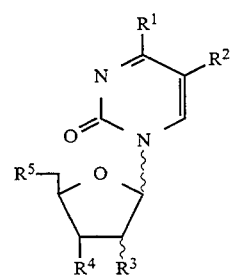

wherein the radicals $R^1$, $R^2$, $R^3$, $R^4$ and $R^5$ are defined as follows:

$R^1$: OH, $NH_2$;

$R^2$:

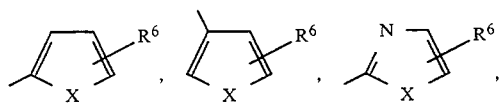

-continued wherein X is O, S, N—$R^7$, Se;

$R^6$ is H, straight or branched $C_{1-10}$ alkyl, F, Cl, Br, I, X—$R^7$, —CH=CH—$R^7$, —C≡C—$R^7$, $CO_2R^7$, $CH_2X$—$R^7$;

$R^7$ is H, straight or branched $C_{1-5}$ alkyl, phenyl;

$R^3$: H, OH, F, $OCH_3$;

$R^4$: H, F, OH or an ether or ester residue thereof, $OCH_3$, CN, C≡CH, $N_3$;

$R^5$: OH or an ether or ester residue thereof;

$$(CH_2)_nP(OM)_2, \quad (CH_2)_n\overset{O}{\underset{OM}{P}}-CH_2-P(OM)_2,$$

wherein n is 0 or 1 and M is hydrogen or a pharmaceutically acceptable counterion such as sodium, potassium, ammonium or alkylammonium; and pharmaceutically acceptable salts thereof.

The invention consequently also refers to the compounds of the formula I for use in therapy. The compounds of the formula I are useful as therapeutic agents in the control and treatment of virus infections in man. The compounds of the formula I are useful as therapeutic agents in the control and treatment of infections caused by hepatitis B virus in mammals and man.

All retroviruses, including HIV, require the enzyme reverse transcriptase in their natural cycle of replication.

Hepatitis B virus (HBV) is a DNA virus with a unique circular double-stranded DNA genome which is partly single-stranded. It contains a specific DNA polymerase required for viral replication. This DNA polymerase also acts as a reverse transcriptase during the replication of HBV DNA via an RNA intermediate.

The compounds of the formula I inhibit the activity of DNA polymerase of hepatitis B virus.

Another important area of use for the compounds of the formula I is in the treatment of herpes virus infections. Among the herpes viruses may be mentioned Herpes simplex type 1 and 2, vericella (Herpes zoster), virus causing infectious mononucleosis (i.e. Epstein-Barr virus), cytomegalovirus and human herpes virus type 6. Important diseases caused by herpes viruses are herpes dermatitis (including herpes labialis), herpes genitalis, herpes keratitis, herpes encephalitis and herpes zoster.

The invention further provides:

A pharmaceutical composition comprising a compound of the formula I as an active ingredient and a pharmaceutically acceptable carrier, including liposomes; and A method for therapeutic treatment of virus infections in an animal or human host in need of treatment comprising administering an effective amount of a compound of the formula I.

It is a preferred aspect of the invention to treat infections caused by herpes viruses and hepatitis B virus.

The nucleoside analogues of the invention are composed of a 5-substituted uracil or cytosine base and a sugar moiety which can for instance be ribose, 2'-deoxyribose, 2',3'-dideoxyribose, arabinose, or analogues thereof.

Preferred compounds of the formula I are those wherein $R^2$ is 2-furyl, 2-thienyl, selenienyl, thiazolyl, 2-(1-alkyl)pyrrolyl or methoxyphenyl;

$R^3$ is hydrogen, hydroxy or fluoro;

$R^4$ is hydrogen, hydroxy, fluoro, cyano or azido; and $R^5$ is hydroxy, a mono-, di- or triphosphate thereof or $$\overset{O}{\underset{}{CH_2P(OM)_2}},$$

wherein M is a pharmaceutically acceptable counterion.

Examples of especially preferred compounds are those of the formula I wherein

| R¹ | R² | R³ | R⁴ | R⁵ |
|----|----|----|----|----|
| OH | 2-furyl | H | OH | OH or triphosphate |
| OH | 2-thienyl | H | OH | OH or triphosphate |
| OH | 2-selenienyl | H | OH | OH or triphosphate |
| OH | 2-thiazolyl | H | OH | OH or triphosphate |
| OH | 2-furyl | OH | OH | OH or triphosphate |
| OH | 2-thienyl | OH | OH | OH or triphosphate |
| OH | 2-selenienyl | OH | OH | OH or triphosphate |
| OH | 2-thiazolyl | OH | OH | OH or triphosphate |
| OH | 2-furyl | OH | F | OH or triphosphate |
| OH | 2-thienyl | OH | F | OH or triphosphate |
| OH | 2-selenienyl | OH | F | OH or triphosphate |
| OH | 2-thiazolyl | OH | F | OH or triphosphate |
| OH | 2-furyl | OH | N₃ | OH or triphosphate |
| OH | 2-thienyl | OH | N₃ | OH or triphosphate |
| OH | 2-selenienyl | OH | N₃ | OH or triphosphate |
| OH | 2-thiazolyl | OH | N₃ | OH or triphosphate |
| OH | 2-furyl | H | H | OH or triphosphate |
| OH | 2-thienyl | H | H | OH or triphosphate |
| OH | 2-selenienyl | H | H | OH or triphosphate |
| OH | 2-thiazolyl | H | H | OH or triphosphate |
| OH | 2-furyl | H | F | OH or triphosphate |
| OH | 2-thienyl | H | F | OH or triphosphate |
| OH | 2-selenienyl | H | F | OH or triphosphate |
| OH | 2-thiazolyl | H | F | OH or triphosphate |
| OH | 2-furyl | H | N₃ | OH or triphosphate |
| OH | 2-thienyl | H | N₃ | OH or triphosphate |
| OH | 2-selenienyl | H | N₃ | OH or triphosphate |
| OH | 2-thiazolyl | H | N₃ | OH or triphosphate |
| OH | 2-furyl | H | OH | methylphosphonate |
| OH | 2-thienyl | H | OH | methylphosphonate |
| OH | 2-thiazolyl | H | OH | methylphosphonate |
| OH | 2-furyl | H | H | methylphosphonate |
| OH | 2-thienyl | H | H | methylphosphonate |
| OH | 2-thiazolyl | H | H | methylphosphonate |
| OH | 2-furyl | H | F | methylphosphonate |
| OH | 2-thienyl | H | F | methylphosphonate |
| OH | 2-thiazolyl | H | F | methylphosphonate |
| OH | 2-furyl | H | N₃ | methylphosphonate |
| OH | 2-thienyl | H | N₃ | methylphosphonate |
| OH | 2-thiazolyl | H | N₃ | methylphosphonate |
| OH | 2-furyl | OH | F | methylphosphonate |
| OH | 2-thienyl | OH | F | methylphosphonate |
| OH | 2-thiazolyl | OH | F | methylphosphonate |

Esters and ethers of the nucleosides are also included in the invention. Examples of esters are mono-, di- and tri-phosphate esters, carboxylic esters, carbonate esters, carbamate esters and sulphonic esters. The acid part of the esters may have alkyl, aryl or arylalkyl chains, where the aryl functionalities are optionally substituted for example by alkoxy, amino, nitrile, alkyl or sulphonamido groups or by one or more halogen atoms. Examples of other types of derivatives of the nucleosides are alkyl or arylalkyl derivatives of the 5-hydroxyl group. The arylalkyl ether derivatives may be for example benzyl or tri-phenyl methyl and the aryl moiety may be optionally substituted. Furthermore, it is understood that the examples of the pharmaceutically acceptable salts cited below also apply to the various esters of derivatives of the nucleosides of the invention.

In a compound of the formula I $R^5$ as an ether residue can be defined as $OR^8$, wherein $R^8$ is $C_{1-6}$ alkyl, arylakyl optionally substituted with one or more alkoxy, amino, nitrile or sulphamido groups or one or more halogen atoms.

$R^4$ and $R^5$ as an ester residue can be derived from a carboxylic acid $R^9COOH$, a carbonic acid $R^{10}OCOOH$, a double ester of a carbonic acid $R^{10}CO_2CH(R^{11})OCO_2H$, a sulphonic acid $R^{10}SO_2OH$, a carbamic acid $R^{10}NHCOOH$ or a phosphoric acid, wherein $R^9$ is hydrogen, $C_{1-17}$ alkyl, alkoxyalkyl, arylalkyl or aryl, $R^{10}$ is $C_{1-17}$, arylalkyl or aryl, $R^{11}$ is hydrogen or $C_{1-3}$ alkyl and said aryl and arylalkyl groups optionally can be substituted with one or more alkyl, alkoxy, amino, nitrile sulphonamido groups or one or more halogen atoms.

Examples of pharmaceutically acceptable salts of the compounds of formula I include base salts, e.g. derived from an appropriate base, such as alkali metal (e.g. sodium, potassium, alkaline earth metal, e.g. magnesium) salts, ammonium and $NX_4^+$ (wherein X is $C_{1-4}$ alkyl). Physiologically acceptable acid salts include salts of organic carboxylic acids such as acetic, lactic, gluconic, citric, tartaric, maleic, malic, pantothenic, isethionic oxalic, lactobionic and succinic acids; organic sulfonic acids such as methanesulfonic, ethanesulfonic, benzenesulfonic, p-chlorobenzenesulphonic and p-toluenesulfonic acids and inorganic acids such as hydrochloric, hydroiodic, sulfuric, phosphoric and sulfamic acids.

Physiologically acceptable counterions M of the phosphonate groups include inorganic and organic counterions. Inorganic counterions are for example ammonium, sodium, potassium, lithium, magnesium and calcium. Organic counterions are derived from non-toxic bases, such as primary, secondary and tertiary amines, including naturally occuring amines. Examples of such amines are diethylamine, triethylamine, isopropylamine, ethanolamine, morpholine, 2-diethylaminoethanol, glucosamine, N-methylglucamine, piperazine and dicyclohexylamine.

In clinical practice the pyrimidine derivatives of the formula I will normally be administered orally, by injection or by infusion in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule. The compound may also be used without carrier material. As examples of pharmaceutical preparations may be mentioned tablets, dragees, capsules, granulates, suspensions, elixirs, syrups, solutions, liposomes etc. Usually the active substance will comprise between 0.05 and 20% for preparations intended for injection and between 10 and 90% for preparations intended for oral administration.

In the treatment of patients suffering from hepatitis B virus infections, it will be preferred to administer the compounds by any suitable route including the oral, parenteral, rectal, nasal, topical and vaginal route. The parenteral route includes subcutaneous, intramuscular, intravenous and sublingual administration. The topical route includes buccal and sublingual administration. The dosage at which the active ingredients are administered may vary within a wide range and will depend on various factors such as the severity of the infection, the age of the patient etc., and may have to be individually adjusted. As a possible range for the amount of the compounds of the invention or a physiologically acceptable salt thereof to be administered per day may be mentioned from about 10 mg to about 10,000 mg, preferentially 100–500 mg for intravenous administration and preferentially 100–3000 mg for oral administration.

METHODS OF PREPARATION

The compounds of the invention may be prepared by one of the following general methods, constituting a further aspect of the invention.

A. Condensing a glycoside as comprised in formula I where the hydroxyl groups may be optionally protected to the N-1 position of a pyrimidine derivative, according to known methods described in the literature. Such methods are described for example in "Basic Principles in Nucleic Acid Chemistry", Vol. I (Academic Press, 1974, Ed. P. O. P. Ts'o), in "Nucleoside Analogues, Chemistry, Biology and Medical Applications" (Pharma Press, 1979, Eds. R. T. Walker, E. De Clercq and F. Eckstein).

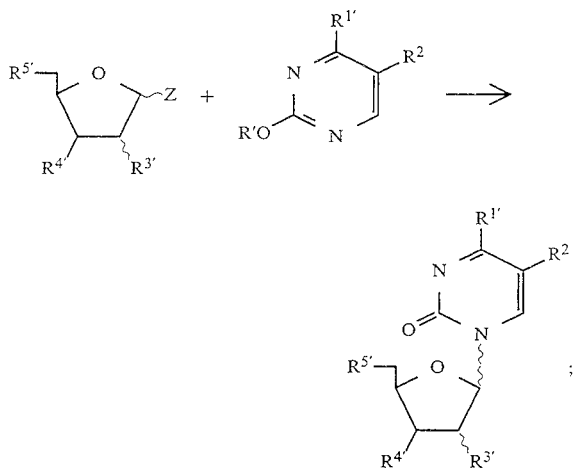

Examples of suitable derivatives of the reacting species are those wherein Z is Cl, Br, I, acyloxy or alkoxy; R' is an alkyl or silyl protecting group, such as $C_2H_5$ or $(CH_3)_3Si$; $R^{1'}$ is $R^1$ as defined above, $OC_2H_5$, $(CH_3)_3SiO$, or $N(COCH_3)Si(CH_3)_2$; $R^2$ is as defined above; $R^{3'}$ and $R^{4'}$ is $R^3$ and $R^4$ respectively as defined above with the proviso that when $R^3$ or $R^4$ is OH said OH must be protected as O-acyl, O-benzoyl, O-benzyl or O-silyl (e.g. dimethyl, tert-butylsilyl); and $R^{5'}$ is $R^5$ as defined above or $OR^8$ wherein $R^8$ is as defined above or silyl (e.g. dimethyl, tert-butylsilyl). After condensation the products may be hydrolyzed or converted by conventional methods, known to those skilled in the art, into compounds of the formula I.

The glycosides are known or may be prepared by suitable adaptions of known methods. The syntheses of a 2,3-dideoxy-3-fluoro-erythro-pentofuranoside for example, has been described by G. W. J. Fleet and J. C. Son in Tetrahedron Letters 40 (1987) pp 3615–3618. The other 3- substitutents may be introduced by methods analogous to those described above and described by N. B. Dyathina and A. V. Azhayev in Syntheses 1984 pp 961–963. The arabinosylglycosides may be prepared by similar methods.

B. The β-anomers of the arabinosyl-pyrimidine nucleoside analogues may be prepared by hydrolysis of the corresponding 2,2'-anhydro nucleoside analogues.

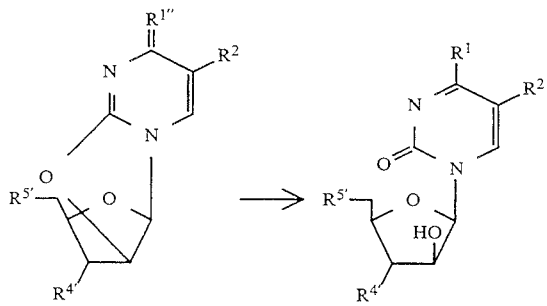

wherein $R^{1''}$ is O or NH and $R^1$, $R^2$, $R^{4'}$ and $R^{5'}$ are as defined above. The hydrolysis may be performed by conventional methods, described in the literature and known to those skilled in the art. It may for example be performed by treating the 2,2'-anhydronucleosides with an aqueous acid.

C. The halogeno, $OCH_3$, $N_3$, CN and C≡CH substituents in the 3'-position of the glycon moiety may be introduced by substitution or a hydroxyl group or a suitably derivatized hydroxyl group

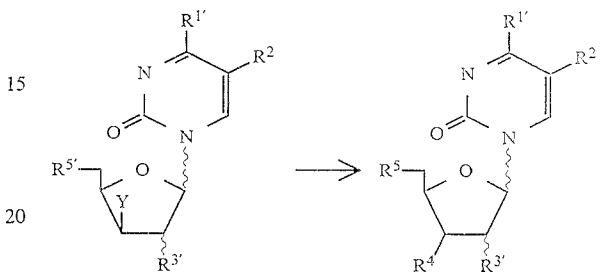

wherein Y is OH or a functionality that will be leaving in the substitution reaction such as for example $CF_3SO_3$; and $R^{1'}$, $R^2$, $R^{3'}$, $R^4$ and $R^{5'}$ are as defined above.

The following examples will further illustrate the invention:

Example 1
1-(2-Deoxy-3,5-di-O-p-toluoyl-alpha-D-ribofuranosyl)-5-(furyl)uracil (VSB 005) and

Example 2
1-(2-Deoxy-3,5-di-O-p-toluoyl-beta-D-ribofuranosyl)-5-(furyl)uracil (VSB 006)

5-(2-Furyl)uracil (150 mg, 0.84 mmol) in hexamethyldisilazane (10 ml) was heated at reflux for 5 hours together with chlorotrimethylsilane (10 drops) and ammoniumsulfate (a few mg). The solution was filtered and evaporated in vacuo to dryness to give bis-trimethylsilylated 5-(2-furyl)uracil (240 mg) as a crude product. This crude product was dissolved in acetonitrile (15 ml, dried over molecular sieves) and added to a solution of 2-deoxy-3,5-di-O-p-toluoyl)-D-arythro-pentosyl chloride (331 mg, 0.85 mmoles; prepared according to C. C. Bhat in Synthetic Procedures in Nucleic Acid Chemistry, Vol. 1, p. 521, Interscience Publ. 1968; W. W. Zorbach and R. S. Tipson eds.) in dried acetonitrile (20 ml) and stirred over night at ambient temperature under an athmosphere of nitrogen. The solution was filtered, evaporated in vacuo and the residue was separated by chromatography on a column of silica to give pure samples of the alpha-anomer (62 mg) and of the beta-anomer (29 mg, m.p. 190°–192° C.). Thin layer chromatography (silica, dichloromethane-ethylacetate 5-1) $R_f$: alpha 0.37; beta 0.50.

Example 3
1-(2-Deoxy-3,5-di-O-p-toluoyl-alpha-D-ribofuranosyl)-5-(2-thienyl)uracil (VSB 128) and

Example 4
1-(2-deoxy-3,5-di-O-p-toluoyl-beta-D-ribofuranosyl)-5-(2-thienyl)uracil (VSB 125)

5-(2-Thienyl)uracil (0.97 g, 5 mmol) in hexamethyldisilazane (10 ml) was heated at reflux for about 2.5 hours together with chloro trimethylsilane (10 drops) and ammoniumsulfate (a few mg). The solution was filtered and evaporated in vacuo to dryness to give bis-trimethylsilylated 5-(2-thienyl)uracil, which was dissolved in 1,2-dichloroethane (25 ml, dried over molecular sieves) and added to a solution of 2-deoxy-3,5-di-O-p-toluoyl)-D-erythro-pentosyl chloride (1.55 g, 4 mmoles; prepared according to C. C. Bhat in Synthetic Procedures in Nucleic Acid Chemistry, Vol. 1, p. 521, Interscience Publ. 1968; W. W. Zorbach and R. S. Tipson eds.) in dry, 1,2-dichloroethane (25 ml). Molecular sieves (2 g, 4 Å) was added and the mixture was stirred at ambient temperature over night after which it was filtered. The solution was washed with an aqueous, saturated solution of sodium bicarbonate (50 ml) and water (50 ml), dried over sodium sulfate, concentrated to a volume of about 25 ml and refrigerated. The precipitate was filtered and recrystallized from 1,2-dichloroethane to give pure β-anomer (0.70 g). The remaining combined solutions were evaporated and the residue was separated on a column of silica eluted with chloroform-ethyl acetate 5-1, to give the pure alpha-anomer, VSA 128, (0.51 g, m.p. 201°–3° C.) and the pure beta-anomer, VSA 125, (total combined yield 0.86 g, m.p. 217°–9° C.). Thin layer chromatography (silica, chloroform-ethyl acetate 5-1) $R_f$: alpha 0.23; beta 0.30.

Analysis for $C_{29}H_{26}N_2O_7S$; calculated (found) %: alpha: C 63.72 (63.5); H 4.80 (4.8); N 5.13 (5.0); beta: C63.72 (63.2); H 4.80 (4.8); N 5.13 (5.1).

Analogous to examples 1 and 2, table 1 lists some further examples which are characterized as shown in table 2.

TABLE 1

Examples of 1-(2-deoxy-3,5-di-O-p-toluoyl-alpha/beta-D-ribofuranosyl)-5-$R^2$-uracil compounds

| Example | alpha/beta | $R^2$ |
|---|---|---|
| 1 | alpha | 2-furyl |
| 2 | beta | 2-furyl |
| 3 | alpha | 2-thienyl |
| 4 | beta | 2-thienyl |
| 5 | alpha | 3-furyl |
| 6 | alpha | 3-thienyl |
| 7 | beta | 3-thienyl |

TABLE 1-continued

Examples of 1-(2-deoxy-3,5-di-O-p-toluoyl-alpha/beta-D-ribofuranosyl)-5-$R^2$-uracil compounds

| Example | alpha/beta | $R^2$ |
|---|---|---|
| 8 | alpha | 2-selenienyl |
| 9 | beta | 2-selenienyl |
| 10 | alpha | 3-selenienyl |
| 11 | beta | 3-selenienyl |
| 12 | alpha | 2-pyridyl |
| 13 | alpha | 3-pyridyl |
| 14 | alpha | 4-pyridyl |
| 15 | alpha | 2-(5-methyl)thienyl |
| 16 | beta | 2-(5-methyl)thienyl |
| 17 | alpha | 2-(5-hexyl)thienyl |
| 18 | beta | 2-(5-hexyl)thienyl |
| 55 | alpha | 2-trans-tioften |
| 56 | beta | 2-trans-tioften |
| 57 | alpha | 2-cis-tioften |
| 58 | beta | 2-cis-tioften |
| 59 | alpha | 2-methoxyphenyl |
| 60 | beta | 2-methoxyphenyl |
| 61 | alpha | 3-methoxyphenyl |

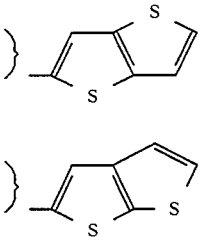

TABLE 2

Data for 1-(2-deoxy-3,5-di-O-P-toluoyl-alpha/beta-D-ribofuranosyl)-5-$R^2$-uracil compounds

| Example | $^{13}$C NMR (CDCl$_3$)δ 1' | 2' | 3' | 4' | 5' | $^1$H NMR (CDCl$_3$)δ 1' | m.p. °C. | Thin layer chromatography $R_f$ |
|---|---|---|---|---|---|---|---|---|
| 1 | 88.1 | 39.4 | 74.9 | 85.8 | 64.3 | 6.44 d | | 0.37 a |
| 2 | 85.8 | 38.7 | 75.1 | 83.3 | 64.7 | 6.53 t | | 0.50 a |
| 3 | 88.0 | 39.2 | 74.6 | 85.7 | 64.0 | 6.41 d | 201–3 | 0.23 b |
| 4 | 85.9 | 38.8 | 75.0 | 83.5 | 64.4 | 6.48 t | 217–9 | 0.30 b |
| 5 | 88.1 | 39.3 | 74.8 | 85.8 | 64.2 | 6.33 d (J 3.5 Hz) | 179–81 | 0.20 b |
| 6 | | | | | | | | |
| 7 | | | | | | | | |
| 8 | | | | | | | 182–4 | 0.22 b |
| 9 | | | | | | | 214–6 | 0.33 b |
| 10 | | | | | | | | |
| 11 | | | | | | | | |
| 12 | 88.1 | 39.5 | 74.5 | 85.5 | 64.0 | 6.11 d (J 3.1 Hz) | | 0.12 a |
| 13 | 88.1 | 39.2 | 74.8 | 85.8 | 64.1 | 6.41 d | | |
| 14 | | | | | | 6.44 | | 0.10 c |
| 15 | 88.0 | 39.2 | 74.8 | 85.7 | 64.2 | 6.41 d (J 3.3 Hz) | | 0.17 d |
| 16 | 85.7 | 38.6 | 75.0 | 83.2 | 64.4 | 6.46 t | | 0.26 d |
| 17 | 88.0 | 39.3 | 74.8 | 85.8 | 64.2 | 6.40 d (J 2.8 Hz) | | 0.22 d |
| 18 | 85.7 | 38.5 | 75.0 | 83.2 | 64.4 | 6.49 t (J 2.0 Hz) | | 0.34 d |
| 55 | | | | | | | 98–101 | 0.57 a |
| 56 | | | | | | | 213–217 | 0.70 a |
| 57 | | | | | | | 111–115 | 0.41 a |
| 58 | | | | | | | 215–218 | 0.54 a |
| 59 | | | | | | | 88–90 | 0.23 a |
| 60 | | | | | | | 196–198 | 0.55 a |
| 61 | | | | | | | 167–169 | 0.28 a | a) CH$_2$Cl$_2$—EtOAc 5-1; b) CHCl$_3$—EtOAc 5-1; c) CHCl$_3$—EtOAc 4-1; d) CHCl$_3$—EtOAc 9-1.

Example 19
1-(2-Deoxy-alpha-D-ribofuranosyl)-5-(2-furyl)uracil (VSB 007)

VSB 005 (62 mg, 0.117 mmol) was suspended in methanol (15 ml, dried over molecular sieves) and sodium methoxide in methanol (1.2 ml, 0.2M) was added. The mixture was stirred at ambient temperature under an athmosphere of nitrogen for 24 hours, after which an ion exchanger, Dowex 50 W×8 H$^+$, was added. The solution was filtered and the solvent evaporated in vacuo. The residue was purified on a column of silica eluted with ethyl acetate-ethanol 9-1, to give 1-(2-deoxy-α-D-ribofuranosyl)-5-(2-furyl)uracil 32 mg (93%). Thin layer chromatography (silica, ethyl acetate-ethanol 18-1) $R_f$: 0.42.

Example 20
1-(2-Deoxy-beta-D-ribofuranosyl)-5-(2-furyl)uracil VSB 008

VSB 006 (29 mg, 0.55 mmol) was hydrolyzed with sodium methoxide as described for VSB 005. After completion of reaction, the dry residue of the crude product was triturated with hexane and purified on silica to give 1-(2-deoxy-β-D-ribofuranosyl)-5-(2-furyl)uracil. The thin layer chromatography (silica, ethyl acetate-ethanol 18-1) $R_f$: 0.47.

Example 21
1-(2-Deoxy-alpha-D-ribofuranosyl)-5-(2-thienyl)uracil (VSB 134)

VSA 128 (0.35 g, 0.64 mmol) was dissolved in methanol (50 ml) and sodium methoxide in methanol (5 ml, 0.2M) was added. The solution was stirred at ambient temperature over night, after which it was neutralized with Dowex 50W×8 H+. The solution was filtered, evaporated in vacuo and the residue was triturated with diethyl ether to give as a solid residue 1-(2-deoxy-α-D-ribofuranosyl)-5-(2-thienyl)uracil. Thin layer chromatography (silica, chloroform-methanol 85-15) $R_f$: 0.44. Analysis for $C_{13}H_{14}N_2O_5S$, calculated (found) %: C 50.31 (50.3); H 4.55 (4.5); N 9.03 (8.8).

Example 22
1-(2-Deoxy-beta-D-ribofuranosyl)-5-(2-thienyl)uracil (VSA 133)

The title compound was prepared from VSA 125 (0.55 g, 1 mmol) in the same way as has been described for the corresponding alpha-anomer VSA 134. Thin layer chromatography for VSA 133 (silica, chloroform-methanol 85-15) $R_f$: 0.47.

Analogous to examples 19–22, table 3 lists some further examples which were characterized as shown in table 4.

TABLE 3
Examples of 1-(2-deoxy-alpha/beta-D-ribofuranosyl)-5-$R^2$ uracil compounds

| Example | alpha/beta | $R^2$ |
|---|---|---|
| 19 | alpha | 2-furyl |
| 20 | beta | 2-furyl |
| 21 | alpha | 2-thienyl |
| 22 | beta | 2-thienyl |
| 23 | alpha | 3-furyl |
| 24 | alpha | 3-thienyl |
| 25 | beta | 3-thienyl |
| 26 | alpha | 2-selenienyl |
| 27 | beta | 2-selenienyl |
| 28 | alpha | 3-selenienyl |
| 29 | alpha | 2-pyridyl |
| 30 | alpha | 3-pyridyl |
| 31 | alpha | 4-pyridyl |
| 32 | alpha | 2-(5-methyl)thienyl |
| 33 | beta | 2-(5-methyl)thienyl |
| 34 | alpha | 2-(5-hexyl)thienyl |
| 35 | beta | 2-(5-hexyl)thienyl |
| 62 | alpha | 2-trans-tioften 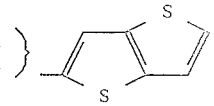 |
| 63 | beta | 2-trans-tioften |
| 64 | alpha | 2-cis-tioften 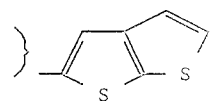 |
| 65 | beta | 2-cis-tioften |

TABLE 4
Data for 1-(2-deoxy-alpha/beta-D-ribofuranosyl)-5-$R^2$-uracil compounds

| Example | $^3$C NMR δ 1' | 2' | 3' | 4' | 5' | $^1$NMR δ 1' | Thin layer chromatography $R_f$ | m.p. °C. |
|---|---|---|---|---|---|---|---|---|
| 19 | 91.9 | 42.2 | 72.9 | 89.2 | 63.8 a | 6.35 dd (J 2.9; 1 Hz)a | 0.42 c | |
| 20 | 89.4 | 42.0 | 72.5 | 87.3 | 63.1 a | 6.44 t (J 3.3 Hz)a | 0.47 c | |
| 21 | 92.1 | 42.1 | 73.0 | 89.0 | 63.9 a | 6.24 dd (J 2.9; 1.0 Hz)b | 0.44 d | |
| 22 | 87.8 | 40.6 | 70.3 | 85.1 | 61.2 b | 6.23 t (J 3.3 Hz)b | 0.47 d | |
| 23 | 90.2 | 41.7 | 72.8 | 88.3 | 63.6 a | 6.37 dd (J 3; 1 Hz)a | 0.44 e | |
| 24 | | | | | | | | |
| 25 | | | | | | 6.36 t (J 5 Hz) a | | |
| 26 | | | | | | | 0.23 f | |
| 27 | | | | | | | 0.29 f | |
| 28 | | | | | | 6.29 dd (J 5; 1 Hz)a | | |
| 29 | 91.7 | 42.2 | 72.8 | 89.5 | 63.7 a | 6.33 dd (J 1.1; 1.5 Hz)a | 0.43 g | |
| 30 | 92.1 | 42.1 | 73.0 | 89.1 | 63.9 a | 6.30 d (J 3.2 Hz)a | | |
| 31 | 90.1 | | 70.9 | 86.6 | 62.0 b | 6.13 dd (J 3.0; 0.8 Hz)b | 0.15 h | |
| 32 | 90.0 | 40.2 | 71.0 | 86.3 | 62.1 b | 6.10 d (J 3.7 Hz)b | | |
| 33 | 87.8 | 40.5 | 70.3 | 84.9 | 61.2 b | 6.23 t (J 3.4 Hz)b | | |
| 34 | 90.0 | 40.2 | 71.0 | 86.3 | 62.1 b | 6.10 d (J 3.1 Hz) | | |
| 35 | 87.8 | 40.5 | 70.3 | 84.9 | 61.2 b | 6.24 t (J 3.3 Hz) | | |
| 62 | | | | | | | | 140 (dec.) |
| 63 | | | | | | | | 242 (dec.) |
| 64 | | | | | | | | 227 (dec.) |
| 65 | | | | | | | | 240 (dec.) |

Additional data for 1-(2-deoxy-alpha/beta-D-ribofuranosyl)-5-$R^2$-uracil compounds

| Example | Elemental analysis Calculated (found) % | | |
|---|---|---|---|
| | C | H | N |
| 25 × 1 H$_2$O | 47.54 | 4.91 | 8.53 |
| | (47.7) | (4.5) | 8.5 |
| 28 × 0.5 H$_2$O | 42.63 | 4.13 | 7.65 |
| | (42.7) | (4.0) | (7.7) | a) CD$_3$OD; b) DMSO-d$_6$ c) EtOAc—EtOH 18-1 d) CHCl$_3$—MeOH 85-15 e) EtOAc—EtOH 9-1 f) CHCl$_3$—MeOH 7-1 g) CHCl$_3$—MeOH 5-1 h) EtOAc—MeOH 9-1

Example 36
1-(2,3-Dideoxy-α-D-ribofuranosyl)-5-(2-thienyl)uracil (VSB 533)

1-(2,3-Dideoxy-5-O-tert-butyldiphenylsilyl-αD-ribofuranosyl-5-(2-thienyl)uracil (0.15 g) was dissolved in tetrahydrofuran, 1M in tetrabutylammonium fluoride (3 ml) and stirred at ambient temperature for 1 hour. The solvent was evaporated and the product was purified by separation on preparative thin layer chromatography (silica—1 mm, ethyl acetate-methanol 9-1) to give 1,(2,3-dideoxy-α-D-ribofuranosyl)-5-(2-thienyl)uracil. TLC (silica, ethyl acetate-methanol 9-1) Rf 0.54.

Example 37
1-(2,3-Dideoxy-β-D-ribofuranosyl)-5-(2-thienyl)uracil (VSB 534)

Starting from 1-(2,3-Dideoxy-5-O-tert-butyldiphenylsilyl-βD-ribofuranosyl-5-(2-thienyl)uracil (0.35 g) and using the same reaction conditions as described for the corresponding α-anomer in example 36, the title compound was obtained. TLC (silica, ethyl acetate-methanol 9-1) Rf 0.59.

The starting materials for the α- and β-anomers of 1-(2,3-dideoxy-D-ribofuranosyl)-5-(2-ethenyl)uracil (examples 36 and 37 respectively) were prepared by the following sequence of reactions a–e.

a) S-γ-tert-Butyldiphenylsilyloxymethyl-γ-butyrolactone (VSB 526)

S-(+)-γ-Trityloxymethyl-γ-butyrolactone (25 g) was mixed with 80% acetic acid (aq, 400 ml) and stirred at 70°–90° C. for 2 hours. The solvent was evaporated in vacuo and the residue was chromatographed on a column of silica, eluted with ethyl acetate-hexane 1-2, to afford S-γ-hydroxymethyl-γ-butyrolactone (VSC 525) as an oil (7.24 g, 90%). This product was dissolved in dry dimethyl formamide (600 ml), imidazole (10.6 g) followed by tert-butyl-diphenylchlorosilane (25 ml, 25.7 g) were added and the solution was stirred at ambient temperature for 4 hours and then at 60° C. for another hour. The solvent was evaporated in vacuo, the residue was dissolved in ethyl acetate, the solution was extracted with water and brine, dried (MgSO4) and the solvent was evaporated in vacuo. The residue was purified by chromatography on a column of silica (ethyl acetate-hexane, 1-4) to yield S-γ-tert-butyldiphenylsilyloxymethyl-γ-butyrolactone (16.9 g, 77%) m.p. 76.5°–77° C.

b) 2,3-Dideoxy-5-O-tert-butyldiphenyl-silyl-D-ribofuranose (VSB 527)

S-γ-tert-Butyldiphenylsilyloxymethyl-γ-butyrolactone (17.1 g) in dry diethyl ether (200 ml) was cooled to −78° C. and stirred while diisobutylaluminum hydride in hexane (75 ml, 1.1M) was added during 15–20 minutes. The stirring was continued for 1 hour at −78° C. after which methanol (35 ml) was added and the reaction solution was allowed to come to room temperature. An aqueous sodium potassium tartrate solution (30%, 150 ml) was added with stirring. The organic phase was separated and extracted with the tartrate salt solution (4×75 ml). The combined aqueous portions were extracted with diethyl ether (4×75 ml). The combined organic solutions were dried (MgSO4) and the solvent was evaporated to give 2,3-dideoxy-5-O-tert-butyldiphenylsilyl-D-ribofuranose (16.3 g) as a viscous clear oil.

c) 1-Acetyl-2,3-dideoxy-5-O-tert-butyldiphenylsilyl-D-ribofuranoside (VSB 528)

Acetic anhydride (15 ml) was added dropwise to an ice-cooled solution of 2,3-dideoxy-5-O-tert-butyldiphenylsilyl-D-ribofuranose (7.58 g) in dry pyridine (25 ml). The stirring was continued at room temperature for 14 hours after which the reaction solution was poured onto ice and extracted with diethyl ether. The ether solution was washed with water, followed by a saturated aqueous sodium hydrogencarbonate solution, water and brine and then dried (MgSO4). The solvent was evaporated to give 1-acetyl-2,3-dideoxy-5-O-tert-butyldiphenylsilyl-D-ribofuranoside as a slightly yellow oil (6.90 g, 89%).

d) 1-Dideoxy-5-O-tert-butyldiphenylsilyl-α-D-ribofuranosyl-5-(2-thienyl)uracil (VSB 530) and e) 1-(2,3-Dideoxy-5-O-tert-butyldiphenylsilyl-β-D-ribofuranosyl-5-(2-thienyl)uracil (VSB 529)

5-(2-Thienyl)uracil (0.85 g) was suspended in hexamethyldisilazane (30 ml) and chlorotrimethylsilane (0.5 ml) and heated at 90° C. overnight together with a small amount of ammoniumsulfate. The solvent was evaporated in vacuo and the residual bis-trimethylsilyated 5-(2-thienyl)uracil was dissolved in dry acetonitrile (10 ml) together with 1-acetyl-2,3-dideoxy-5-O-tert-butyldiphenylsilyl-D-ribofuranoside (1.75 g). The solution was cooled to −35° C. and SnCl4 (1.14 g, 0.51 ml) in dry acetonitrile (5 ml) was added dropwise. The reaction temperature was raised to −15° C. and an excess of ammonia in methanol was added. The solution was allowed to reach room temperature, the solvent was evaporated in vacuo; the residue was extracted with ethyl acetate, filtered, the solvent was again evaporated in vacuo and the residue was subjected to chromatography on a column of silica eluted with ethyl acetate-hexane 1-9, to give the α- and β-anomers of 1-dideoxy-5-O-tert-butyldiphenylsilyl-D-ribofuranosyl-5-(2-thienyl)uracil.

α-anomer: 0.18 g TLC (silica, ethyl acetate-hexane, 1-1) Rf 0.42. $^{13}$C NMR (CDCl$_3$)δ: 26.20 (C3'); 26.98 (CH$_3$); 32.7 (C2'); 65.80 (C5'); 81.68 (C4'); 86.87 (C1')); 109.78 (C5); 125.40, 126.93, 127.2, 133.2 (thienyl); 127.76, 127.88, 129.98, 135.64 (phenyl); 133.6 (C6); 149.67 (C2); 162 (C4).

β-anomer: 0.38 g, TLC (silica, ethyl acetate-hexane, 1-1) Rf 0.60. $^{13}$C NMR (CDCl$_3$)δ: 26 (C3'); 27 (CH$_3$); 33 (C2'); 66 (C5'); 82 (C4'); 88.5 (C1'); 125, 127, 133 (thienyl); 128, 130, 136 (phenyl); 134 (C6).

Example 38
1-(2,5,6-Trideoxy-α-D-ribo-hexofuranosyl-6-phosphonic acid)-5-(2-thienyl)uracil (VSB 823)

1-(2,5,6-Trideoxy-6-diemthylphosphono-α-D-ribo-hexofuranosyl)-5-(2-thienyl)uracil (214 mg) was heated at reflux in hexamethyl-disilazane (5 ml) and acetonitrile for about 15 minutes until all material was dissolved. The solvent was evaporated, bromotrimethylsilane (0,2 ml) in acetonitrile (5 ml) was added and the solution was stirred at ambient temperature for 3 hours. Aqueous ammonia (25%, 5 ml) was added, the solvent was evaporated and the residue was dissolved in water-dimethyl sulfoxide (about 1 ml). After filtration trifluoroacetic acid (10 drops) and acetone (5 ml) was added, the precipitate was collected and washed (decanted) with acetone (3×5 ml), to yield 1-(2,5,6-trideoxy-α-D-ribo-hexofuranosyl-6-phosphonic acid)-5-(2-thienyl)-uracil. TLC (polyethylene imine, Macherey-Nagel, 0.2M LiCl, molybdate spray-reagent) Rf 0.15.

Example 39
1-(2,5,6-Trideoxy-β-D-ribo-hexofuranosyl-6-phosphonic acid)-5-(2-thienyl)uracil (VSB 822)

Starting from 1-(2,5,6-trideoxy-6-dimethyl-phosphono-β-D-ribo-hexofuranosyl-5-(2-thienyl)uracil (170 mg) and using the same reaction conditions as described for the corresponding α-anomer (example 38), the title compound was obtained (40 mg). TLC (polyethylene imine, Macherey-Nagel, 0.2M LiCl, molybdate spray reagent) Rf 0.15. $^{13}$C NMR (DMSO-d6)δ: 22.70, 25.45 (C5'); 26.96 (C6'); 39.86 (C2'); 72.06 (C3'); 85.75 (C1'); 88.64, 88.98 (C4'); 108.10 (C5'); 122.99, 126, 126.83, 134.55 thienyl); 138 (C6'); 149.82 (C2'); 161.62 (C4').

The starting materials for the α- and β-anomers of 1-(2,5,6-trideoxy-D-ribo-hexofuranosyl-6-phosphonic acid)-5-(2-thienyl)-uracil (examples 38 and 39 respectively) were prepared by the following reaction sequence (a–h).

a) Methyl-2-deoxy-3-O-p-toluoyl-5-O-tert-butyldiphenylsilyl-D-ribofuranoside

Imidazole (18.9 g) and tert-butyldiphenyl-chlorosilane (37.7 g) were added to methyl-2-deoxyribofuranoside (20.3 g) dissolved in dimethylformamid (150 ml) and the solution was stirred at ambient temperature over night. Thin layer chromatography (TLC, silica, ethyl acetate-hexane 1-4) shows the reaction product methyl-2-deoxy-5-O-tert-butyldiphenylsilyl-D-ribofuranoside with Rf 0.2. The solvent was evaporated in vacuo, the residue was dissolved in diethyl ether washed with water (4×50 ml), dried (MgSO$_4$) and the solvent was evaporated to give a residue (47.1 g). The residue was dissolved in pyridine (200 ml), p-toluoylchloride (21.18 g) was added and the solution was stirred at ambient temperature for about 1 hour after which the solvent was evaporated in vacuo, the residue was taken up in diethyl ether and washed with water. The solution was dried (MgSO$_4$) and the solvent was evaporated in vacuo to give the title compound (50 g). TLC (silica, etyl acetate-hexane 1-4) Rf 0.5. $^{13}$C NMR (CDCl$_3$)δ: 21.77 (CH$_3$, p-tol.); 26.73, 26.90 (CH$_3$, tert-but.); 39.41 (C2); 55.41 (OCH$_3$); 65.02 (C5); 75.85 (C3); 84.29 (C4); 105.77 (C1); 127.78, 128.34, 129.17, 129.60, 129.77, 134.96, 135.73 (C, phenyl).

b) Methyl-2-deoxy-3-O-p-toluoyl-D-ribofuranoside (VSB 818)

Methyl-2-deoxy-3-O-p-toluoyl-5-O-tert-butyldiphenylsilyl-D-ribofuranoside (50 g) was dissolved in a 1M solution of tetrabutyl-ammonium fluoride in tetrahydrofuran (100 ml). Dry sodium hydrogencarbonate (1 eq, 137 mmol) was added and the mixture was stirred at ambient temperature over night; after which the solvent was evaporated, the residue was washed with water and purified by chromatography on a silica column, eluted with ethylacetate-hexane (1-4), followed by ethyl acetate, to give the title compound (16.65 g). TLC (silica, ethyl acetate-hexane), 1-4) Rf 0.1. $^{13}$C NMR (CDCl$_3$) δ: 21.80 (CH$_3$, p-tol.); 40.14 (C2); 55.68 (OCH$_3$); 64.10 (C5); 75.97 (C3); 86.35 (C4); 105.84 (C1); 129.24, 129.70, 129.80, 129.93 (C, phenyl).

c) Diphenyl (1-methyl-2,5,6-trideoxy-3-O-p-toluoyl-D-ribo-hex-5-enofuranos-6-yl)-phosphonate (VSB 818)

Pyridinium trifluoroacetate (1.89 g) prepared from equimolar amounts of pyridine and trifluoroacetic acid in diethyl ether) and some molecular sieves (4 Å) were added to a solution of methyl-2-deoxy-3-O-p-toluoylfuranoside (5.26 g) in dimethylsulfoxide (40 ml). The solution was stirred at ambient temperature for about 30 minutes after which dicyclohexylcarbodiimide (12.2 g) was added and the stirring was continued at 60° C. for 3 hours. TLC (silica, ethyl acetate-hexane, 1-4) shows a positive reaction with dinitrophenyl hydrazin-sulfuric acid spray at Rf 0.1. Methanol (20 ml) was added and stirring was continued at 60° C. for another hour, after which methanol was evaporated in vacuo, the solution was filtered, diphenyl[(triphenylphosphoranylidene)-methyl]phosphonate [9 g; G. H. Jones, E. K. Hamamura, J. Moffat, Tetrahedron Lett. (1968), 5371; J. A. Montgomery, A. G. Laseter, K. Hewson, J. Heterocyclic Chem. 11 (1974) 211] was added and the solution was stirred at 70° C. for 3 hours. After cooling, diethyl ether (200 ml) was added, the solution was washed with water (4×100 ml) and the ether solution was evaporated to dryness. The residue was purified by chromatography on a column of silica (500 g) eluted with ethyl acetate-hexane 1-4, yielding 4.4 g of diphenyl(1-methyl-2,5,6-trideoxy-3-O-p-toluoyl-D-ribo-hex-5-enofuranos-6-yl)phosphonate. $^{13}$C NMR (CDCl$_3$) δ: 21.70 (CH$_3$, p-tol); 37.85 (C2); 56.00 (OCH$_3$); 77.45 (C3); 83.78, 84.24 (C4); 106.52 (C1); 115.33, 119.12 (C5); 152.40, 152.52 (C6); 165.97 (CO).

d) Diphenyl(1-methyl-2,5,6-trideoxy-3-O-p-toluoyl-D-ribo-hexofuranos-6-yl)phosphonate (VSB 819)

Diphenyl(1-methyl-2,5,6-trideoxy-3-O-p-toluoyl-D-ribo-hex-5-enofuranos-6-yl)phosphonate (4.46 g) in dry tetrahydrofurane was hydrogenated at 1 bar for 30 minutes using Pd/C (5%) as a catalyst. The reaction mixture was filtered through a celite pad, the solvent was evaporated and the residue was purified by chromatography, on silica to give the title compound (3.72 g). $^{13}$C NMR (CDCl$_3$) δ: 21.53 (CH$_3$, p-tol); 21.21, 24.06 (C5); 27.68 (C6); 38.95 (C2); 55.27 (OCH$_3$); 77.52 (C3); 83.68, 84.04 (C4); 105.50 (C1); 166.02 (CO).

e) 1-(2,5,6)-Trideoxy-3-O-p-toluoyl-6-diphenylphosphono-α-D-ribo-hexofuranosyl)-5-(2-thienyl)uracil (VSB 826) and f) 1-(2,5,6)-Trideoxy-3-O-p-toluoyl-6-diphenylphosphono-β-D-ribo-hexofuranosyl)-5-(2-thienyl)uracil (VSB 820)

5-(2-thienyl)uracil (0.5 g) in dry acetonitrile (15 ml), hexamethyl disilazane (5 ml) and chlorotrimethyl silane (0.5 ml) was heated at reflux for about 30 minutes after which the solvent were evaporated to give 2,4-bis-trimethyl silylated 5-(2-thienyl)uracil. Dry acetonitrile was added, followed by diphenyl(1-methyl-2,5,6-trideoxy-3-O-p-toluoyl-D-ribo-hexofuranos-6-yl)phosphonate (VSB 819, 1.65 g) in dry acetonitrile (10 ml) and finally tert-butyl-dimethylsilyltriflate (0.6 ml) under vigorous stirring, and the solution was stirred at ambient temperature for about 1.5 hours, after which concentrated aqueous ammonia (4 ml) was added). The solvent was evaporated in vacuo and the residue was purified by chromatography in a column of silica (100 g) eluted with ethyl acetate-hexane, 1-1, to give the α-anomer (0.56 g) and the β-anomer (0.40 g) of 1-(2,5,6-trideoxy-3-O-p-toluoyl-6-diphenyl-phosphono-D-ribo-hexofuranosyl)-5-(2-thienyl)uracil. TLC (silica, ethyl acetate-hexane, 1-1) Rf: α 0.15; β 0.20. $^{13}$C NMR (CDCl$_3$) δ, α-anomer: 20.12 (CH$_3$, p-tol.); 19.68, 22.53 (C5'); 25.40, 25.47 (C6'); 36.81 (C2'); 76.50 (C3'); 85.84, 86.16 (C4'); 86.35 (C1'); 108.22 (C5'); 122.89, 124.23, 125.49 thienyl); 134.03 (C6); β-anomer: 21.80 (CH$_3$, p-tol.); 21.21, 24.08 (C5'); 27.08 (C6'); 37.27 (C2'); 76.48 (C3'); 84.12, 84.48 (C4'); 85.70 (C1'); 110.75 (C5'); 124.76, 125.62, 127.17 (thienyl); 133.86 (C6).

g) 1-(2,5,6)-Trideoxy-6-dimethylphosphono-α-D-ribo-hexofuranosyl)-5-(2-thienyl)uracil (VSB 825)

1-(2,5,6-Trideoxy-3-O-p-toluoyl-6-diphenylphosphono-α-D-ribohexofuranosyl-5-(2-thienyl)uracil (444 mg) was dissolved in 0.5M sodium methoxide in methanol (20 ml) and stirred at ambient temperature for 3 hours. The solution was neutralized with Dowex 50W×8 (pyridinium+), filtered and the solvent was evaporated. Silica and diethyl ether-hexane was added, the solvent was decanted and the residue was again triturated with ether-hexane (4×). Finally the silica was eluted with methanol-tetrahydrofuran 1-1 and the solvent was evaporated in vacuo to give the title compound (234 mg). $^{13}$C NMR (CD$_3$OD) δ: 18.95, 21.80 (C5'); 25.98, 26.08 (C6'); 39.75 (C2'); 52.49 (2 POCH$_3$); 73.32 (C3'); 86.28 (C1'); 88.25, 88.57 (C4'); 109.29 (C5); 123.79; 125.10, 126.59, 133.88 (thienyl); 136.59 (C6); 149.92 (C2); 161.91 (C4).

h) 1-(2,5,6)-Trideoxy-6-dimethylphosphono-β-D-ribo-hexofuranosyl)-5-(2-thienyl)uracil (VSB 824)

Starting from 1-(2,5,6-trideoxy-3-O-p-toluoyl-6-diphenylphosphono-β-D-ribo-hexofuranosyl)-5-(2-thienyl)uracil (326 mg) and using essentially the same reaction conditions as described for the α-anomer, the title compound was obtained. In the work-up procedure for the β-anomer no silica was included; instead the crude product was dissolved in diethyl ether and by addition of hexane the product precipitated (190 mg). $^{13}$C NMR (CDCl$_3$-DMSO-d6) δ: 18.90, 21.75 (C5'); 25.98, 26.08 (C6'); 39.43 (C2'); 52.08 (2 POCH$_3$); 73.05 (C3'); 85.38, 85.45, 85.80 (C1', C4'); 109.78 (C5); 123.86, 125.13, 126.52, 133.13 (thienyl); 134.57 (C6); 149.38 (C2); 162 (C4);

The precursor 5-substituted pyrimidine compounds of the formula I',

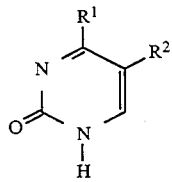

wherein the radicals R$^1$ and R$^2$ are defined as follows:
R$^1$: OH, NH$_2$;
R$^2$:

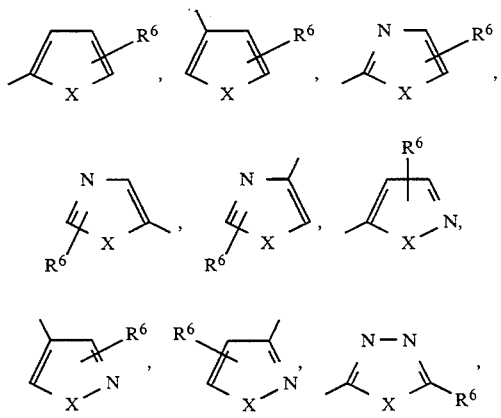

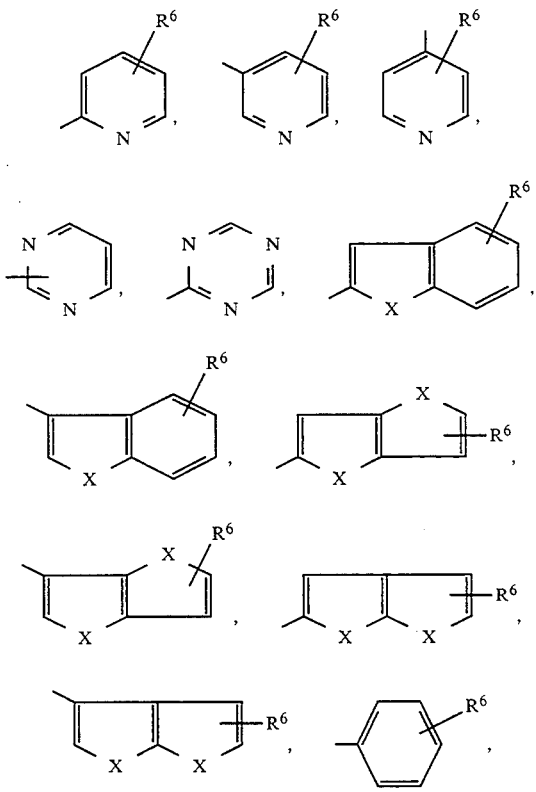

wherein X is O, S, N—R$^7$, Se;

R$^6$ is H, straight or branched C$_{1-10}$ alkyl, F, Cl, Br, I, X—R$^7$, —CH=CH—R$^7$, —C≡C—R$^7$, CO$_2$R$^7$, CH$_2$X—R$^7$;

R$^7$ is H, straight or branched C$_{1-5}$ alkyl, phenyl; constitute a further aspect of the invention.

The compounds of the formula I' may be prepared by the following general method:

The 2,4-dialkoxy-5-halopyrimidine compound may be reacted with the boronic acid or trialkylstannyl derivative of the heterocycle; alternatively the 2,4-dialkoxy-5-boronic acid pyrimidine or 2,4-dialkoxy-5-trialkylstannyl pyrimidine may be reacted with the halogen derivative of the heterocycle. In all cases the reaction is catalyzed by a palladium complex and performed in an organic solvent such as for example tetrahydrofuran or 1,2-dimethoxyethane at a temperature from −20° to 100° C. or at reflux for a period of 5 minutes to 2 days. After completion of the condensation reaction and work-up of the reaction mixture the 2,4-dialkoxy groups of the pyrimidine compound are hydrolyzed by acidic hydrolysis by known methods.

The 5-substituted uracil base or the 5-substituted uridine analogue may be converted to a 5-substituted cytosine base or cytidine analogue by conventional methods, the principles of which have been described for example by W. L. Sung (J. Chem. Soc. Chem. Commun. 1981, p. 1089 and J. Organic Chemistry 1982, volyme 47, pages 3623–3628) and by P. Herdewijn et al. (J. Medicinal Chemistry 1985, volyme 28, pages 550–555).

The following examples will further illustrate the precursor compounds of the invention.

Example 40  5-(5'-Chloro-2'-thienyl)uracil

A 250 ml flask was charged with 3.41 g (0.010 mole) of 2,4-di-tert butoxy-5-(5'-chloro-2'-thienyl)pyrimidine, 60 ml of methanol and 60 ml of 4M hydrochloric acid and the reaction mixture was stirred at room temperature for 30 min. The precipitate crystals were collected by filtration, washed with methanol and dried giving an almost quantitative yield of the title compound, mp over 300° C.

Anal. Found C 42.1, H 2.20, N 12.25, S 14.2. Calc. for $C_8H_5ClN_2O_2S$ (228.6): C 42.02, H 2.20, N 12.25, S 14.02.

The starting material, 2,4-di-tert.butoxy-5-(5'-chloro-2'-thienyl)pyrimidine, was prepared as follows:

A 100 ml flask equipped with condenser, magnetic stirrer and nitrogen inlet was charged with 1.65 g (0.010 mol) of 2-bromo-5-chlorothiophene, 0.3 mmol of tetrakis(triphenylphosphine)-palladium(0) and 50 ml 1,2-dimethoxyethane. After stirring for 10 min, 2.95 g (0.011 mole) of 2,4-di-tert.butoxy-5-pyrimidineboronic acid was added immediately followed by 20 ml of 1M sodium carbonate solution. The reaction mixture was refluxed for 4 hours with vigorous stirring under nitrogen. After cooling to room temperature the traces of the catalyst were filtered off, the organic solvent was evaporated under reduced pressure and the residue was diluted with water and extracted with three portions of ether. The combined etheral phases were washed with water, saturated sodium chloride solution and dried over magnesium sulphate. The solvent was evaporated and the residue purified by flash-chromatography on silica gel giving 2.6 g (76%) of 2,4ditert.butoxy-5-(5'-chloro-2'-thienyl)pyrimidine mp 82.0°–83.5° C.

Anal. Found C 56.4, H 6.24, N 8.16, S 9.52. Calc. for $C_{16}H_{21}ClN_2O_2S$ (340.9): C 56.37, H 6.21, N 8.22, S 9.41.

Example 41  5-(3'-furyl)uracil

A 100 ml flash was charged with 1.45 g (5.0 mmole) of 2,4-di-tert.butoxy-5-(3'-furyl)pyrimidine dissolved in 25 ml of methanol and 25 ml of 5M hydrochloric acid and the mixture was stirred at room temperature for 30 min. The precipitated crystals were collected by filtration, washed with methanol and dried giving the title compound in almost quantitative yield, melting with decomposition above 250° C.

Anal. C 54.1, H 3.34, N 15.5, O 27.2. Calc. for $C_8H_6N_2O_3$ (178.1): C 53.9, H 3.39, N 15.7, O 26.9.

The starting material 2,4-di-tert.butoxy-5-(3'-furyl)-pyrimidine was prepared as follows:

A 250 ml flask equipped with condenser, magnetic stirrer and nitrogen inlet was charged with 7.3 g (0.024 mole) of 5-bromo-2,4-di-tert-butoxypyrimidine, 0.75 mmol of tetrakis(triphenylphosphine)palladium (0) and 80 ml of 1,2-dimethoxyethane. After stirring for 10 min 3.0 g (0.027 mole) of 3-furanboronic acid was added, immediately followed by 60 ml of 1M sodium carbonate solution. The reaction mixture was refluxed for 4 hours with vigorous stirring under nitrogen. After cooling to room temperature, the traces of catalyst were filtered off, the organic solvent was evaporated under reduced pressure and the residue diluted with water and extracted with three 50 ml portions of ether. The combined etheral phases were washed with water, saturated sodium chloride solution and dried over magnesium sulphate. The ether was evaporated and the residue was purified by flash chromatography using hexane-ethyl acetate (4:1) as eluent, yielding 4.1 g (59%) of the title compound as an oil.

Anal. Found C 66.5, H 7.68, N 9.64, O 17.0. Calc. for $C_{16}H_{22}N_2O_3$ (290.4) C 66.2, H 7.64, N 9.65, O 16.5.

Example 42  5-[2'-(N-methyl)pyrrolyl]uracil 3.0 g (9.9 mmole) of 2,4-di-tert.butoxy-5-[2'-(N-methyl)pyrrolyl]-pyrimidine was stirred with 40 ml of methanol and 40 ml of 5M hydrochloric acid for 30 min. The precipitated crystals were collected by filtration, washed with methanol and water and dried, yielding 1.5 g (79%) of the title compound melting with decomposition over 250° C.

Anal. Found C 56.0, H 4.70, N 22.00. Calc. for $C_9H_9H_3O_2$ (191.2): C 56.5, H 4.47, N 22.0.

The starting material 2,4-di-tert.butoxy-5-[2'-(N-methyl)pyrrolyl]pyrimidine was prepared as follows:

A 250 ml flask equipped with condenser, magnetic stirrer and nitrogen inlet was charged with 9.0 g (29.7 mmole) 2,4-di-tert-butoxy-5-bromopyrimidine. 1.05 g (1.50 mmole) of $PdCl_2[P(C_6H_5)_3]_2$ and 8.0 g (32.7 mmole) of N-methyl-2-trimethylstannylpyrrole in 80 ml of anhydrous tetrahydrofuran and refluxed for 20 hours. After cooling the reaction mixture, it was diluted with 200 ml of ether and washed twice with 50 ml of water. After drying with magnesium sulphate and evaporating the solvent, the compound was purified by chromatography using "silicagel 60" and a mixture of pentane-ether (9:1) as eluent, yielding 3.5 g (39%) of the title compound, mp 113°–114° C.

Anal. Found C 67.0, H 8.37, N 13.7. Calc. for $C_{17}H_{25}N_3O_2$ (303.4) C 67.3, H 8.30, N 13.8.

Analogous to example 40, table 5 gives some further examples of preparations from 2,4-di-tert.-butoxy-5-pyrimidine boronic acid and a bromo substituted heterocyclic compound. Their characteristics are given in table 6.

TABLE 5

Examples of 5-$R^2$-uracil compounds

| Example | $R^2$ | Intermediate 2,4-di-tert-butoxy-5-($R^2$) pyrimidine yield % | mp °C. | 5-$R^2$-uracil yield |
|---|---|---|---|---|
| 40 | 2-(5-chloro)thienyl | 76 | 82–83.5 | 86 |
| 43 | 2-(5-methyl)thienyl | 50 | 65–68 | 93 |
| 44 | 2-(5-hexyl)thienyl | 52 | oil | 90 |
| 45 | 2-furyl | 49 | 87–88 | 100 |
| 46 | 2-thiazolyl | 49 | 102–103 | 100 |
| 47 | 5-thiazolyl | 62 | 68–69 | 100 |
| 48 | 2-pyridyl | 60 | 128–129 | 100 |
| 49 | 3-pyridyl | 69 | 88–89 | 100 |
| 50 | 4-pyridyl | 70 | 92–93 | 100 |
| 51 | 2-methoxyphenyl | 35 | 90-91.5 | 90 |
| 52 | 3-methoxyphenyl | 65 | 93–94 | 90 |
| 53 | 4-methoxyphenyl | 41 | 92–94 | 90 |
| 54 | 2,5-dimethoxyphenyl | 47 | 91–93 | 100 |
| 66 | 2-trans-tioften | 57 | 108–110 | |
| 67 | 2-cis-tioften | 60 | 108–110 | |
| 68 | 3-trans-tioften | 55 | 105–107 | |
| 69 | 3-cis-tioften | 27 | 88–90 | |

TABLE 6

$^1$H NMR chemical shifts (ppm, in DMSO-$d_6$) for 5-substituted uracil compounds

| Example | NH | NH | H6 | H2' | H3' | H4' | H5' | H6' | $CH_3$ | $OCH_3$ | $OCH_3$ | $CH_2$ |
|---|---|---|---|---|---|---|---|---|---|---|---|---|
| 40 | 11.5 | | 8.07 | | 7,03 | 7.33 | — | — | | | | |

TABLE 6-continued

| | | | | | $^1$H NMR chemical shifts (ppm, in DMSO-$d_6$) for 5-substituted uracil compounds | | | | | | | |
|---|---|---|---|---|---|---|---|---|---|---|---|---|
| Example | NH | NH | H6 | H2' | H3' | H4' | H5' | H6' | CH$_3$ | OCH$_3$ | OCH$_3$ | CH$_2$ |
| 43 | | 9.3 | 7.83 | — | 7.22 | 6.71 | — | — | 2.51 | | | 2.73 a |
| 44 | 11.39 | 11.20 | 7.83 | — | 7.24 | 6.73 | — | — | | | | |
| 45 | 11.40 | 11.20 | 7.71 | — | 6.83 | 6.57 | 7.62 | | | | | |
| 46 | 11.85 | 11.78 | 8.55 | — | — | 7.92 | 7.71 | — | | | | |
| 47 | 11.56 | 11.61 | 8.22 | 9.11 | — | 8.39 | — | — | | | | |
| 48 | 11.90 | 11.74 | 8.49 | — | 8.67 | 8.20 | 7.58 | 8.33 | | | | |
| 49 | 11.69 | 11.58 | 8.13 | 9.12 | — | 8.70 | 7.98 | 7.76 | | | | |
| 50 | 12.00 | 11.66 | 8.43 | 8.77 | 8.37 | — | 8.37 | 8.77 | | | | |
| 51 | 11.17 | 10.97 | 7.38 | — | 7.03 | 7.30 | 6.93 | 7.20 | | 3.73 | | |
| 52 | | 11.20 | 7.65 | 7.13 | — | 6.86 | 7.26 | 7.13 | | | | |
| 53 | 11.19 | 11.02 | 7.53 | 7.48 | 6.94 | — | 6.90 | 4.75 | | 3.76 | | |
| 54 | 11.17 | 10.95 | 7.39 | — | 6.95 | 6.85 | — | 6.85 | | 3.70 | 3.67 | | a) Additional bands at δ 1.64; 1.32; 0.88 with the relative intensities 2:6:3

Biological Tests

Test I Effect of compounds of the formula I on HIV in H9 cells

Materials and methods: HIV infection of H9 cells

H9 cells, $10^5$ cells per well on a 24 well plate, suspended in 2 ml RPMI-medium containing 10% fetal calf serum, 100 μg/ml penicillin, 10 μg/ml streptomycin sulfate and 2 μg/ml polybrene are exposed to HIV (HTLV-III$_B$) and different concentrations of the test compounds. The plates are incubated at 37° C. in 5% $CO_2$ for 6-7 days. The contents in each well is then homogenized with a pipette and transferred to a centrifuge tube. After centrifugation for 10 min at 1500 rpm the supernatant is removed and the cell pellet is analyzed by fixing in methanol on glass plates. Human HIV positive serum diluted 1:80 or 1:160 is added and incubated for 30 min at 37° C. The plate is then washed with phosphate-buffered saline (PBS) containing $Ca^{2+}$ and $Mg^{2+}$. Sheep antihuman conjugate (FITC) is added and after a new incubation the plate is again washed with PBS. Contrast staining is done with Evans blue and after drying the frequency of HIV antigen containing cells is determined in a microscope. The test result is shown in Table 7.

TABLE 7

| | Concentration (μM) for 50% inhibition (IC$_{50}$) of human immuno deficiency virus multiplication in cell culture 1-(2'-deoxy-α/β-D-ribofuranosyl)-5-R$^2$-uracil | | |
|---|---|---|---|
| α/β | R$^2$ | Code | IC$_{50}$ M |
| α | 2-thienyl | VSA 134 | 0.05–10 |
| α | 2-selenienyl | VSA 188 | 2–20 |
| α | 3-selenienyl | VSA 996 | 3–100 |
| α | 2-furyl | VSB 007 | <10 |
| α | 2-(5-methylthienyl) | VSB 515 | 10–>10 |
| β | 3-selenienyl | VSA 992 | 5–>10 |
| β | 2-thienyl | VSA 189 | 10–>10 |
| β | 2-furyl | VSB 008 | 10–>10 |

Table 7 shows that the tested compounds are active inhibitors of HIV virus multiplication.

Test II Cellular toxicity

H9 cells, $2 \times 10^7$ cells per plate, are incubated in RPMI-1640 medium containing 10% fetal calf serum, 70 mg/l penicillin, 100 mg/l streptomycin and 10 mM hepes, in absence or presence of test compounds. The number of cells per plate is determined after 48 h. Cells incubated in the absence of test compounds then underwent two cell division cycles.

F5000 cells, which are human embryo cells, $1 \times 10^5$ cells per plate, are incubated in Eagle's minimal essential medium, supplemented with Earle's salts, non-essential amino acids, 10% fetal calf serum, 10 mM hepes, 70 mg/l penicillin and 100 mg/l streptomycin, in absence or presence of test compounds. The number of cells per plate is determined after 48 h. Cells incubated in the absence of test compounds underwent one cell division cycle. The results are given as % inhibition of cell multiplication when the concentration of the compound is 100μM or 250μM. The test results are given in table 8.

TABLE 8

| | Cellular toxicity on H9 and F5000 cells 1-(2'-deoxy-α/β-D-ribofuranosyl)-5-R$^2$-uracil | | | |
|---|---|---|---|---|
| | | | % inhibition (concentration μM) | |
| α/β | R$^2$ | Code | H9 | F5000 |
| α | 2-thienyl | VSA 134 | 35(250) | 0–35(100) |
| α | 2-selenienyl | VSA 188 | 40(200) | 15(200) |
| α | 3-selenienyl | VSA 996 | 65(200) | 30(200) |
| α | 2-furyl | VSB 007 | | |
| α | 2-(5-methyl)thienyl | VSB 515 | | |
| β | 3-selenienyl | VSA 992 | 40(200) | 0(200) |
| β | 2-thienyl | VSA 189 | 35(200) | 10(100) |
| β | 2-furyl | VSB 008 | | 0(200) |

Table 8 shows that the concentrations at which the compounds exhibit toxicities exceed the concentrations needed for 50% inhibition of HIV multiplication as given in table 7.

Test III Inhibition of reverse transcriptases and DNA polymerases by triphosphates of compounds of the invention The 5'-triphosphates were synthesized essentially as described (Yoshikawa, M, Kato T, Takenishi T, Bull. Chem. Soc. (Japan), 42,3505–3508, 1969; Ludwig, J., Acta Biochim. Biophys. Acad. Sci. Hung. 16, 131–133, 1981; Ruth, J. L., Cheng, Y. C., Mol. Pharmacol. 20, 415 1981.) The HIV-RT was obtained as described by Hansen et al (Hansen J, Schulze T and Moelling K, J. Biol. Chem. 262, 12393–12396, 1987) from cultures of *Escherichia coli* expressing the cloned HIV-pol gene. The HBV-DNAP was prepared from virus obtained from human serum, essentially as described by Nordenfelt et al (1987) [Nordenfelt E, Löfgren B, Chattopadhyaya J., Oberg B, J. Med Virol. 22, 231–236, 1987]. The HSV-2 DNAP and cellular DNAPα preparation and reaction conditions have been described by Larsson et al [Larsson A, Sundqvist A, Parnerud A-M, 1986, Mol. Pharmacol. 29, 614–621]. In reactions using HIV-RT, the enzyme was incubated with the template $(rA)_n(dT)_{12-18}$ and different concentrations of inhibitor and substrate (dTTP) as described by Vrang et al 1987, (Vrang L., Bazin H., Remaud G., Chattopadhyaya J. and Oberg B., Antiviral Res. 7, 139–145, 1987). The hepatitis B virus enzyme activity was determined with a virus preparation solubilized by non-idet P40, and endogenous nucleic acid as template, as described by Nordenfelt et al (vide supra)

TABLE 9

Concentration (uM) for 50% inhibition (IC$_{50}$) of enzymes by triphosphates of some compounds of the invention

| Compound | HIV RT[1] | HBV DNAP[2] | HSV-2 DNAP[3] | DNAPα[4] |
|---|---|---|---|---|
| 1-(2-Deoxy-beta-D-ribofuranosyl)-5-(2-thienyl)uracil-5'-triphosphate | 0.015 | 0.11 | 0.06 | 1,6 |
| 1-(2-Deoxy-alpha-D-ribofuranosyl)-5-(2-thienyl)uracil-5'-triphosphate | 2.0 | 18.0 | 11.0 | 80,0 |

[1] Human immuno deficiency virus reverse transcriptase
[2] Hepatit B virus DNA polymerase
[3] Herpes simplex virus type 2 DNA polymerase
[4] DNA polymerase alpha.

I claim:

1. A compound of the formula

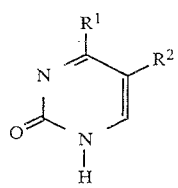

I' wherein R$^1$ and R$^2$ are defined as follows
R$^1$ is OH, NH$_2$;
R$^2$ is

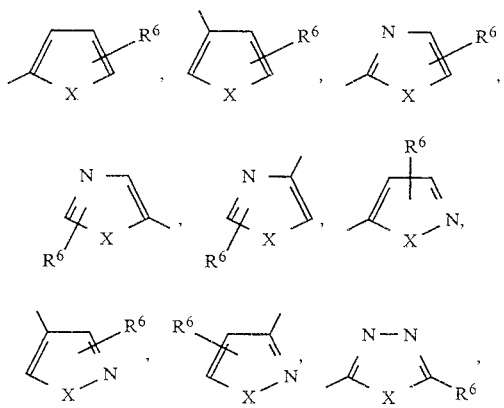

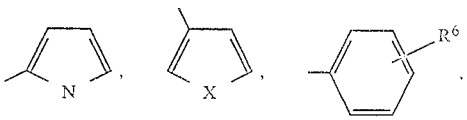

wherein X is O, S, N—R$^7$, Se;
R$^6$ is H, straight or branched C$_{1-10}$ alkyl, F, Cl, Br, I, X—R$^7$, —CH=CH—R$^7$, —C≡C—R$^7$, CO$_2$R$^7$, CH$_2$X—R$^7$;
R$^7$ is H, straight or branched C$_{1-15}$ alkyl, phenyl;
with the provisos that when R$^1$ is OH, R$^2$ is not

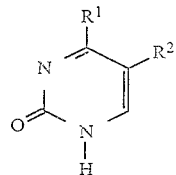

when R$^6$ is H, straight or branched C$_{1-10}$ alkyl, or X—R$^7$ when X is O and R$^7$ is H, or straight or branched C$_{1-15}$ alkyl;
and when R$^1$ is NH$_2$, R$^2$ is not 2. A compound of the formula:

I' wherein R$^1$ and R$^2$ are defined as follows:
R$^1$ is OH, NH$_2$;
R$^2$ is 2-thienyl, 2-seleniynyl, 2-furyl, 2-thiazolyl, 2-(1-methyl)pyrrolyl or methoxyphenyl,
with the proviso that when
R$^1$ is OH,
R$^2$ is not 2-thienyl, 2-seleniynyl or methoxyphenyl.

* * * * *